United States Patent [19]

Laves

[11] 4,162,306

[45] Jul. 24, 1979

[54] MEDICINE FOR TREATING DIARRHEA

[75] Inventor: Hans-Georg Laves, Gehrden near Hannover, Fed. Rep. of Germany

[73] Assignee: Laves-Arzneimittel G.m.b.H. & Co. K.G., Fed. Rep. of Germany

[21] Appl. No.: 894,423

[22] Filed: Apr. 7, 1978

[30] Foreign Application Priority Data

Apr. 6, 1977 [DE] Fed. Rep. of Germany ....... 2715384

[51] Int. Cl.² .............................................. A61K 33/44
[52] U.S. Cl. .................................................... 424/125
[58] Field of Search .......................................... 424/125

[56] References Cited

PUBLICATIONS

*Handbook of Non-Prescription Drugs,* Pub. Amer. Pharm. Assoc., Wash., D.C. (1967), p. 39.

*Primary Examiner*—Frederick E. Waddell
*Attorney, Agent, or Firm*—Cushman, Darby & Cushman

[57] ABSTRACT

There is provided a medicine for treating diarrhea which comprises medicinal carbon, Bolus alba, pectin, sweet whey powder and lactose.

3 Claims, No Drawings

MEDICINE FOR TREATING DIARRHEA

BACKGROUND OF THE INVENTION

The invention is directed to a medicine for treating diarrhea.

By the term diarrhea, there is understood the occurrence of too frequent thinly liquid emptying of the intestine. These illnesses are brought about by hypermotility of the intestine, by disturbances of the secretion as well as disturbances of the resportion in the small and large intestine. The main cause of these disturbances frequently is a change in the contents of the intestine, particularly changes of the normal intestinal flora through colonies of pathogenic germs (bacteria) or germs (bateria) alien to the intestine or through the absorption of toxic substances.

Diarrhea based on change of the characteristic intestinal flora occur particularly frequently in infants, small children and old people since in these the characteristic intestinal flora has an especial sensitivity. Furthermore, not only with this group of people but also with normal adults frequently at specific times of the year there occurs for example through eating unwashed fruit or vegetables the so-called "summer diarrheas" which also frequently occur with tourists based on the change in the diet.

A particular problem is intestinal disturbances with accompanying diarrhea which frequently occur in patients who have been treated with antibiotics and in this connection especially broad spectrum antibiotics such as tetracyclines. The giving of antibiotics can cause damage to or destroy the physiological microbial intestinal flora which then frequently leads to a super infection with staphylococci.

In the initial stage of an acute, not too severe diarrhea even today there is still prescribed a one to two day interruption in eating in which only tea is given, then followed by an increasing diet. At the same time, customarily, there is given a diarrheica which generally after several days leads to an elimination of the symptoms.

Severe, persistent diarrheas signify large losses of water and electrolyte which particularly in infants can lead to life threatening circulatory collapse and then can be intercepted through intravenous salt and sugar infusions, in extreme cases only by plasma transfusions. Therefore, it is absolutely necessary to stop these large water and electrolyte losses as soon as possible.

For a long time it has been customary to treat diarrheas with adsorbents, which include for example carbon (including activated carbon) and Bolus alba (kaolin). Adsorbents bind bacteria, bacterial toxin and local irritating materials by physical reversible fixing on their active surfaces. The medicinal carbon is a so-called activated carbon in which through a specific process there is produced the largest possible effective surface area. The electrically non-charged carbon adsorbs materials independent of their charge, although the adsorption on carbon is dependent on the hydrogen ion concentration. Nondissociated materials are adsorbed substantially better than dissociated materials. The adsorption ratio, however, continuously changes in the gastrointestinal tract so that in spite of the large adsorption capability the carbon there must be reckoned with the fact that a certain portion of the materials adsorbed on the carbon is again freed in the slow passage through the intestine. In spite of its excellent efficacy the medicinal carbon has the particular disadvantage that an activity frequently occurs only after days and that at the same time after the end of the diarrhea frequently there follows a constipation. Bolus alba indeed also has long been known as an adsorbent, of course, it must be given in very large amounts and therefore today is rarely used. Additionally with Bolus alba, it is a matter of negatively charged adsorbent which chiefly can only adsorb positively charged particles and therefore frequently in the treatment of diarrheas is of extremely variable effectiveness.

As adsorbents, particularly for the treatment of diarrheas in infants and older children, there have also been employed for a long time pectin preparations. Pectins are high molecular weight carbohydrate-like plant materials which essentially consist of glycosidically connected galacturonic acid whose acids groups are more or less strongly esterified with methanol (i.e., they are partially methylated polygalacturonic acids). The compounds act as adsorbents in the intestine and are slowly broken down there, whereby acids are apparently formed as breakdown products which create an unfavorable growth medium for the bacteria alien to the intestine.

Also with Bolus alba and pectins there only occurs an effect against the causes of the diarrhea after days so that in spite of the treatment there must be reckoned with high losses of salt and water.

Either because of the uncertain or only slowly established effect of these adsorbents there are preferably employed today for fighting diarrheas synthetic compounds, as for example, amoebicidal or bacteriostatic or bactericidal compounds. For example, these include various difficulty soluble sulfonamides, quinoline derivatives, various antibiotics as for example streptomycin, phenanthroline derivatives, and several nitrofuran derivatives. All of these compounds have in common that besides harming pathogenic germs there also occurs harm to the true intestinal flora with the known results. Furthermore, the greater part of these compounds exhibit considerable further side effects which in part greatly limit their usability.

The invention, therefore, is based on the problem of developing a new medicine against diarrheas which acts quickly and exhibits the least possible side effects.

SUMMARY OF THE INVENTION

To solve this problem, there is proposed in this invention a medicine against diarrheas which contains the active constituents medicinal carbon (activated carbon), Bolus alba, pectin, lactose and sweet whey powder.

Surprisingly it has now been established that a mixture of medicinal carbon, Bolus alba, pectin, sweet whey powder and lactose has a surprisingly quick activity in diarrheas wherein in most cases already the giving several grams of this mixture in the form of a granulate or several tablets is sufficient to stop a starting diarrhea in infants, small children or adults within several hours.

The compounds of the invention are known per se and medicinal carbon, Bolus alba and pectin have already been added alone or in combination for fighting diarrheas. Lactose occurs in all milk and is considered as a very weak laxative which occasionally finds use in the therapy of infant constipation. Also sweet whey powder has previously been employed as a weak laxative. Sweet whey powder contains in addition to lactose and orotates above all a filling of short chain sugars such as trioses, tetroses and pentoses. These saccharides are characterized by a substantial unfermentability. They serve the cellulose cycle as non-replenishing nutrient substrate.

Completely surprising, however, in spite of the effect of the individual constituents was the surprisingly quick and side effect free efficacy of the new agent. In the previous investigations it was able to be shown that with the help of sweet whey there was formed in the cell tissue so-called "sugar streets". These sugar streets take over the function of an electrolyte carrier with simultaneous availability of the nutrient substrate for the cell nucleus.

This surprisingly quick occurrence of effect upon the giving of the agent of the invention cannot be explained by an addition of the known individual effects so that there appears to be a synergistic activity.

For the production of the agent of the invention, there are preferably employed activated carbon and Bolus alba (kaolin) in the qualities which are prescribed in DAB 7 (German Dispensatory 7). The pectin employed preferably has a molecular weight of 99,550 as it is recovered in the usual manner from apple residue with conventional working up. The lactose likewise is preferably worked up into the quality required by DAB 7. The sweet whey powder is recovered by removing albumins and fats from sweet whey from cows.

The agent of the invention, for the most part, contains 15–30% medicinal carbon, 20–40% Bolus alba, 1–3% pectin, 20–40% sweet whey powder and 10–20% lactose. Preferably there is used about 25% medicinal carbon, 30% Bolus alba, 2% pectin, 30% sweet whey powder and 13% lactose.

The agent of the invention can be used in the form of powders, granulates, tablets or suspensions. It can be produced in known manner using conventional assistants. Granulates are preferably employed in microencapsulated form.

Unless otherwise indicated all parts and percentages are by weight.

The composition can comprise, consist essentially of or consist of the stated materials.

The invention will be explained further in connection with the following examples.

DESCRIPTION OF THE PREFERRED EMBODIMENTS

EXAMPLE 1

450 grams of Bolus alba, 450 grams of sweet whey powder and 195 grams of lactose were mixed with the help of a fluidized bed mixture under slow addition of 375 grams of medicinal carbon (activated carbon). Hereby it should be observed that the air supply is finely dosed since otherwise the specific gravity of the medicinal carbon makes more difficult a homogeneous mixing. This powder mixture was subsequently subjected to a spray granulation with addition of 30 grams of pectin having an average molecular weight of 99,550 in water. The thus obtained granulate was subsequently microencapsulated in known manner to improve the flow or pouring behavior and for stabilization of the contents.

EXAMPLE 2

The granulate produced according to claim 1 was pressed in known manner to tablets on rotary tabletting machines. The granulates of Example 1 and the tablets of Example 2 can be administered orally to the patient 1 to 3 times a day with each granulate or tablet containing 0.2 to 1 grams of the composition. Thus for example, there can be employed once a day 3 tablets, each tablet containing 0.5 grams of the composition.

What is claimed is:

1. A medicinal composition suitable for treating diarrhea which comprises 15–30% medicinal carbon, 20–40% Bolus alba, 1–3% pectin, 20–40% sweet whey powder, and 10–20% lactose.

2. A medicinal composition according to claim 1 comprising 25% medicinal carbon, 30% Bolus alba, 2% pectin, 30% sweet whey powder and 13% lactose.

3. A method of treating diarrhea comprising feeding a patient an amount of the composition of claim 1 effective to relieve the symptoms of diarrhea.

* * * * *